(12) United States Patent
Trennepohl

(10) Patent No.: US 6,712,748 B2
(45) Date of Patent: *Mar. 30, 2004

(54) METHOD AND APPARATUS FOR FOLDING A WEB

(75) Inventor: Michael D. Trennepohl, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/308,470

(22) Filed: Dec. 3, 2002

(65) Prior Publication Data

US 2003/0083185 A1 May 1, 2003

Related U.S. Application Data

(63) Continuation of application No. 09/703,742, filed on Nov. 1, 2000.

(51) Int. Cl.$^7$ .................................................. B31F 1/00
(52) U.S. Cl. .................... 493/423; 493/123; 493/125
(58) Field of Search ................................. 493/410, 423, 493/405, 441, 123, 125

(56) References Cited

U.S. PATENT DOCUMENTS

| | | | | |
|---|---|---|---|---|
| 3,829,359 A | * | 8/1974 | Isujibayashi et al. | 162/274 |
| 3,991,631 A | * | 11/1976 | Kapp | 474/200 |
| 4,067,439 A | | 1/1978 | Janitsch | |
| 4,185,737 A | * | 1/1980 | Blattermann | 198/831 |
| 4,526,272 A | | 7/1985 | Peterson | |
| 4,614,512 A | * | 9/1986 | Capdeboscq | 493/441 |
| 4,648,336 A | | 3/1987 | Ragnebring | |
| 4,795,416 A | | 1/1989 | Cogswell et al. | |
| 4,842,130 A | | 6/1989 | Mraz | |
| 4,846,338 A | | 7/1989 | Widmer | |
| 4,850,582 A | | 7/1989 | Newsome | |
| 4,936,087 A | | 6/1990 | Mori et al. | |
| 4,986,413 A | | 1/1991 | Mraz | |
| 5,037,365 A | | 8/1991 | Breton | |
| 5,090,672 A | | 2/1992 | Ballestrazzi et al. | |
| 5,114,001 A | | 5/1992 | Anderson | |
| 5,114,392 A | | 5/1992 | McAdam, III et al. | |
| 5,151,075 A | | 9/1992 | Beaulleu et al. | |
| 5,154,675 A | | 10/1992 | Roovers | |
| 5,178,601 A | | 1/1993 | Lovenbrant | |
| 5,293,988 A | | 3/1994 | Sumino | |
| 5,332,083 A | * | 7/1994 | Axmann | 198/831 |
| 5,375,695 A | | 12/1994 | Daringer et al. | |
| 5,762,597 A | | 6/1998 | Valterio | |
| 5,800,329 A | * | 9/1998 | Fager et al. | 493/417 |
| 5,921,379 A | | 7/1999 | Horton | |
| 5,992,615 A | | 11/1999 | Muchalov | |
| 5,996,861 A | | 12/1999 | Propach | |
| 5,997,459 A | * | 12/1999 | Kruger et al. | 493/441 |

FOREIGN PATENT DOCUMENTS

DE 31 18886 A1 12/1982

* cited by examiner

Primary Examiner—Rinaldi I. Rada
Assistant Examiner—Paul Durand
(74) Attorney, Agent, or Firm—Jack L. Oney, Jr.; Michael S. Kolodesh; Jay A. Krebs

(57) ABSTRACT

A method for making a longitudinal fold in a web, including the steps of: (1) providing a web-supporting device; (2) providing a folding belt disposed adjacent to a first longitudinal edge of the web-supporting device; (3) providing the web which is superimposed onto a web-contacting surface of the web-supporting device such that a first longitudinal edge of the web extends laterally beyond the first longitudinal edge of the web-supporting device and at least partially onto the folding belt; and (4) folding the first longitudinal fold of the web by twisting the folding belt around its longitudinal axis of rotation. The longitudinal axis of rotation of the folding belt extends parallel to the longitudinal fold line of the web.

1 Claim, 12 Drawing Sheets

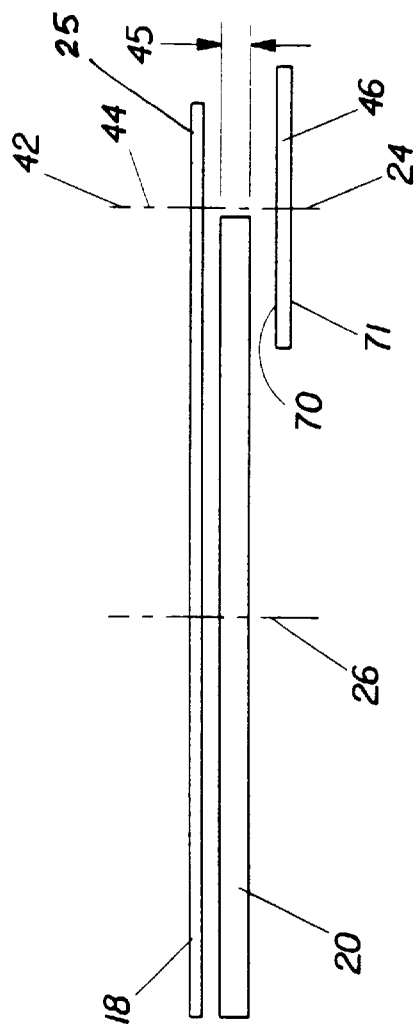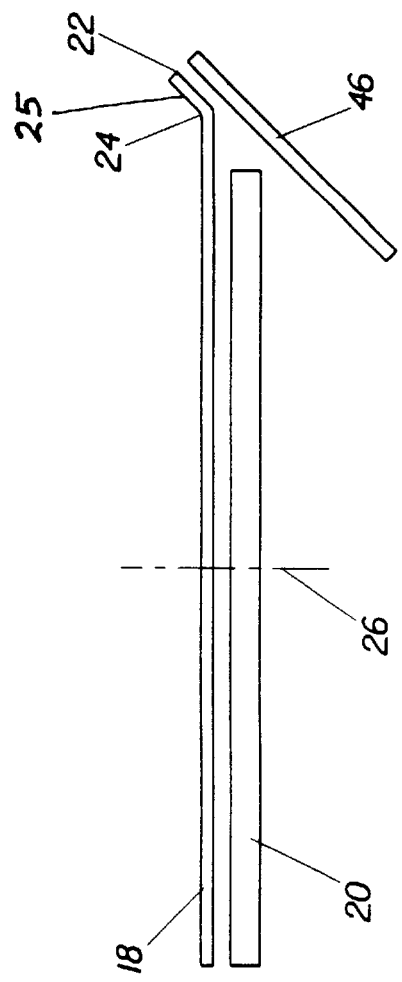

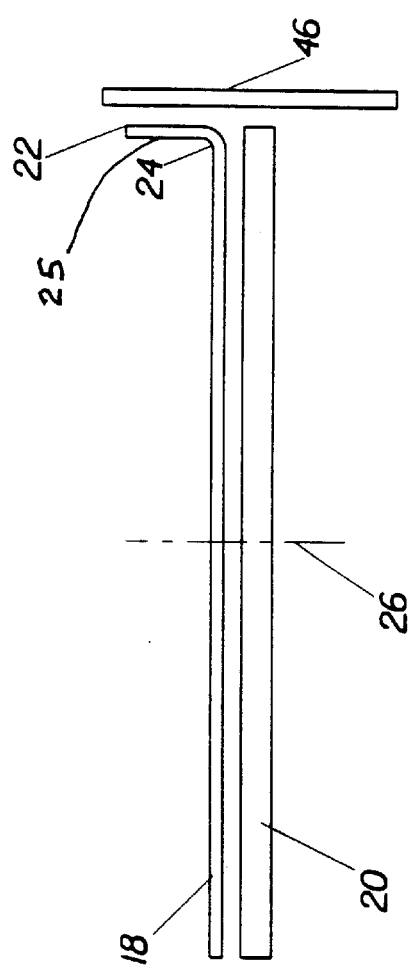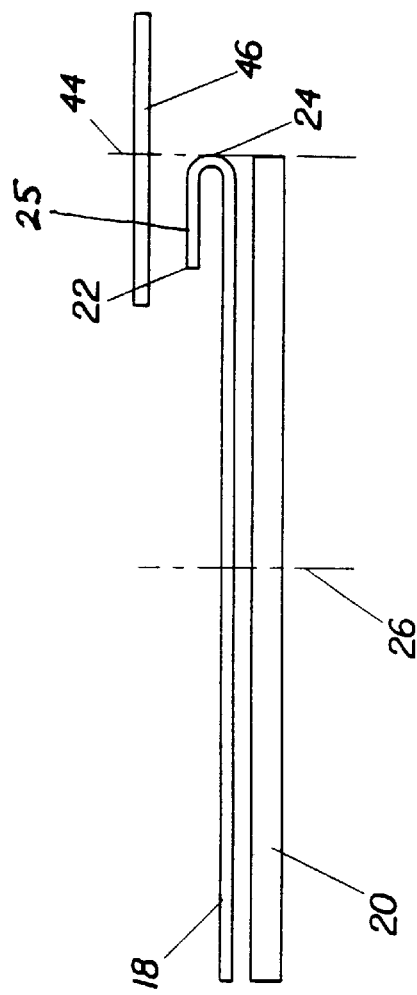

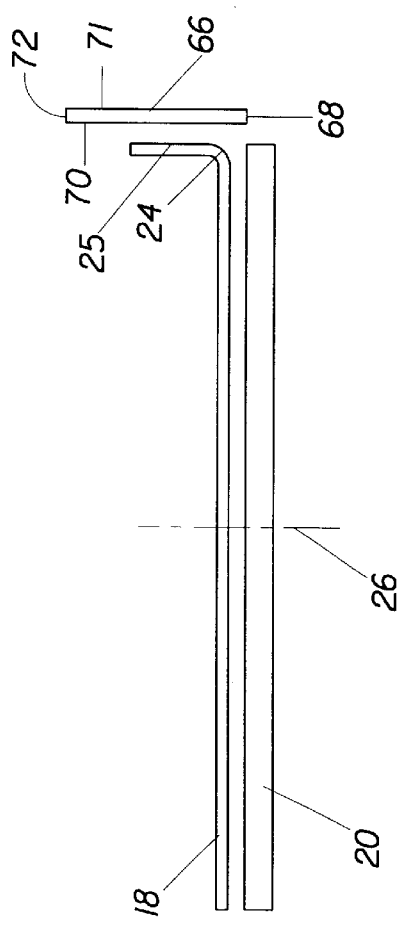
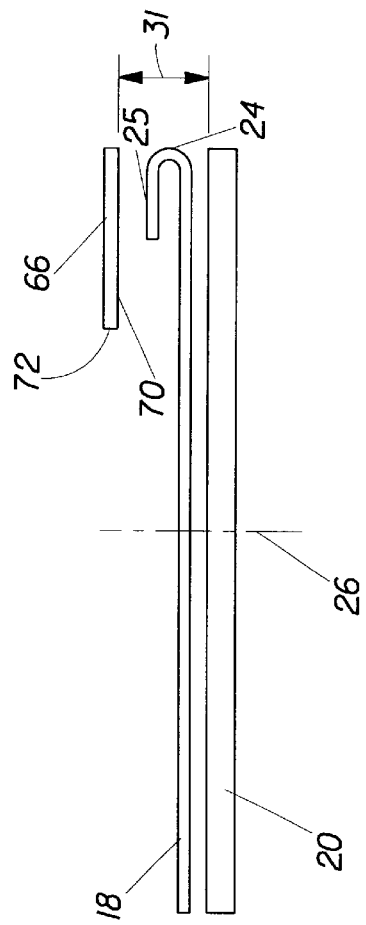

METHOD AND APPARATUS FOR FOLDING A WEB

CROSS REFERENCE TO RELATED APPLICATIONS

This application is a continuation of the copending parent application U.S. Ser. No. 09/703,742 filed Nov. 1, 2000.

FIELD OF THE INVENTION

The present invention relates to a method and an apparatus for folding a web. More particularly, this invention relates to a method and an apparatus for folding a web by use of a continuous twist belt.

BACKGROUND OF THE INVENTION

Conventional methods of making a longitudinal fold in a continuous web material generally employ stationary folding devices, such as rails or folding boards, and active folding devices, such as folding belts, which move with the web in the direction of the web to be folded.

Stationary folding devices, such as rails, are generally used for folding relatively stiff webs having both continuous and/or discontinuous longitudinal edges, and for folding soft, flexible webs having usually only continuous longitudinal edges. Other stationary folding devices, such as folding boards, are generally used for folding soft, flexible webs having usually only continuous longitudinal edges.

Active folding devices, such as folding belts, are generally used for folding both relatively rigid and soft, flexible webs having both continuous or discontinuous longitudinal edges. However, conventional belt folding devices do not work consistently well in folding relatively narrow longitudinal folds in soft, flexible webs.

One type of a conventional folding belt system 10 is illustrated in FIGS. 1–5, wherein the longitudinal axis of rotation 14 of the folding belt 12 is not parallel, (i.e., angled) to the fold line 24 of the web 18. (The term "longitudinal axis of rotation" refers herein to an axis around which a folding belt rotates or twists during folding a web.) In one embodiment, as shown in FIG. 1, the web 18 is disposed to a conveyor belt 20 (or any suitable web-supporting device) and folded inward along the first longitudinal edge 22 of the web 18 creating the fold line 24 and the longitudinally folded flap 25 along the fold line 24. The fold line 24 is substantially parallel to the longitudinal centerline 26 of the conveyor belt 20 and the machine direction 17. (The term "longitudinal centerline" refers herein to a centerline which is equidistant between the opposing longitudinal edges of a belt. The term "machine direction" refers herein to the direction in which the materials being processed move.) The web 18 travels in the first or machine direction 17, and the folding belt 12 travels in the second direction 19, which is angled in relation to the machine direction 17. Further, the longitudinal axis of rotation 14 of the folding belt 12 generally coincides with the longitudinal centerline 16 of the folding belt 12. FIG. 2 illustrates an initial arrangement of the folding belt 12 at a zero rotation position of the folding belt 12 in relation to the conveyor belt 20 and the web material 18, wherein the folding belt 12 is generally coplanar with the conveyor belt 20. FIG. 3 illustrates an intermediate arrangement of the folding belt 12 between the zero rotation position of FIG. 2 and a 90-degree rotation position of FIG. 4. FIG. 5 illustrates a final arrangement of the folding belt 12 in providing the longitudinally folded flap 25 along the fold line 24. As seen in FIGS. 3–4, during rotation of the folding belt 12, the first longitudinal edge 28 of the folding belt 12 loses its contact with the web 18 when the first longitudinal edge 28 rotates around the longitudinal axis of rotation 14 of the folding belt 12, away from the web 18. Furthermore, during this rotation, the web-contacting surface 29 of the folding belt 12 also moves away from the web 18. This relative movement between the web-contacting surface 29 of the folding belt 12 and the web 18 may result in wrinkles in the folding flap 25 and/or in improper fold configurations of the folded flap 25, especially when folding relatively narrow folds in soft, flexible webs.

Another type of a belt folding device is disclosed in U.S. Pat. No. 5,762,597, issued on Jun. 9, 1998 to Valterio. This device employs a folding belt supported by an under-belt track which forces the belt to rotate around an axis which is generally parallel to the machine direction and, thus, to the longitudinal fold line. However, the drawback of this device may be excessive wear of the folding belt and deteriorating quality of the fold due to a drag between the belt and the under-belt track.

Still another type of a belt folding device is disclosed in U.S. Pat. No. 4,795,416 issued on Jan. 3, 1989 to Cogswell et al. The device employs several folding belts disposed consecutively along the web path to fold the web in consecutive stages, wherein each folding belt rotates a portion of a total rotation required for providing a complete fold in a web. The shortcoming of this device may be a gap separating the sequential folding belts, especially, when folding discontinuous longitudinal edges in soft, flexible materials. The discontinuous edges may be caught in the gap and cause jams and/or inconsistency in quality of the folds.

Given the foregoing, there exists a continuing need in the art to provide a folding device for folding relatively narrow longitudinal fold(s), especially discontinuous, relatively narrow longitudinal folds(s) in soft, flexible webs. Further, it would be desirable to provide a folding device having a folding belt without the use of an under-belt track. Such needs are satisfied by the belt folder of the present invention.

SUMMARY OF THE INVENTION

In accordance with one aspect of the present invention, a method is provided for making a longitudinal fold in a web moving in a machine direction. The method generally includes the following steps: (1) providing a web-supporting device having a web-contacting surface and first and second opposing longitudinal edges; (2) providing a simply-supported folding belt disposed adjacent to the first longitudinal edge of the web-supporting device, the simply-supported folding belt includes a first surface contacting the web, a first longitudinal edge and a second longitudinal edge opposed thereto, a width extending between the first and the second longitudinal edges, a longitudinal centerline, and a longitudinal axis of rotation which is generally parallel to the longitudinal centerline; (3) providing the web having a first and a second longitudinal edges opposed to each other, the web being superimposed onto the web-contacting surface of the web-supporting device such that the first longitudinal edge of the web extends laterally beyond the first longitudinal edge of the web-supporting device and at least partially onto the first surface of the simply-supported folding belt; and (4) folding the first longitudinal fold of the web by twisting the simply-supported folding belt around its longitudinal axis of rotation such that the first surface of the simply-supported folding belt rotates toward the first longitudinal edge of the web-supporting device to face at least partially the web-contacting surface of the web-supporting device, wherein the longitudinal axis of rotation of the simply-supported folding belt extends substantially parallel to a longitudinal fold line of the longitudinal fold of the web. Furthermore, the longitudinal axis of rotation of the simply-supported folding belt of the present invention may be offset a distance from the longitudinal centerline, wherein the offset distance is less than half of the width of the simply-supported folding belt or substantially equal to the half of the width of the simply-supported folding belt or greater than half of the width of the simply-supported folding belt.

BRIEF DESCRIPTION OF THE DRAWINGS

FIG. 7 is a cross-sectional view along cut line 7—7 of FIG. 6.

FIG. 8 is a cross-sectional view along cut line 8—8 of FIG. 6.

FIG. 9 is a cross-sectional view along cut line 9—9 of FIG. 6.

FIG. 10 is a cross-sectional view along cut line 10—10 of FIG. 6.

FIG. 14 is a cross-sectional view along cut line 14—14 of FIG. 11.

FIG. 15 is a cross-sectional view along cut line 14—14 of FIG. 11.

DETAILED DESCRIPTION OF THE INVENTION

Figure 1:
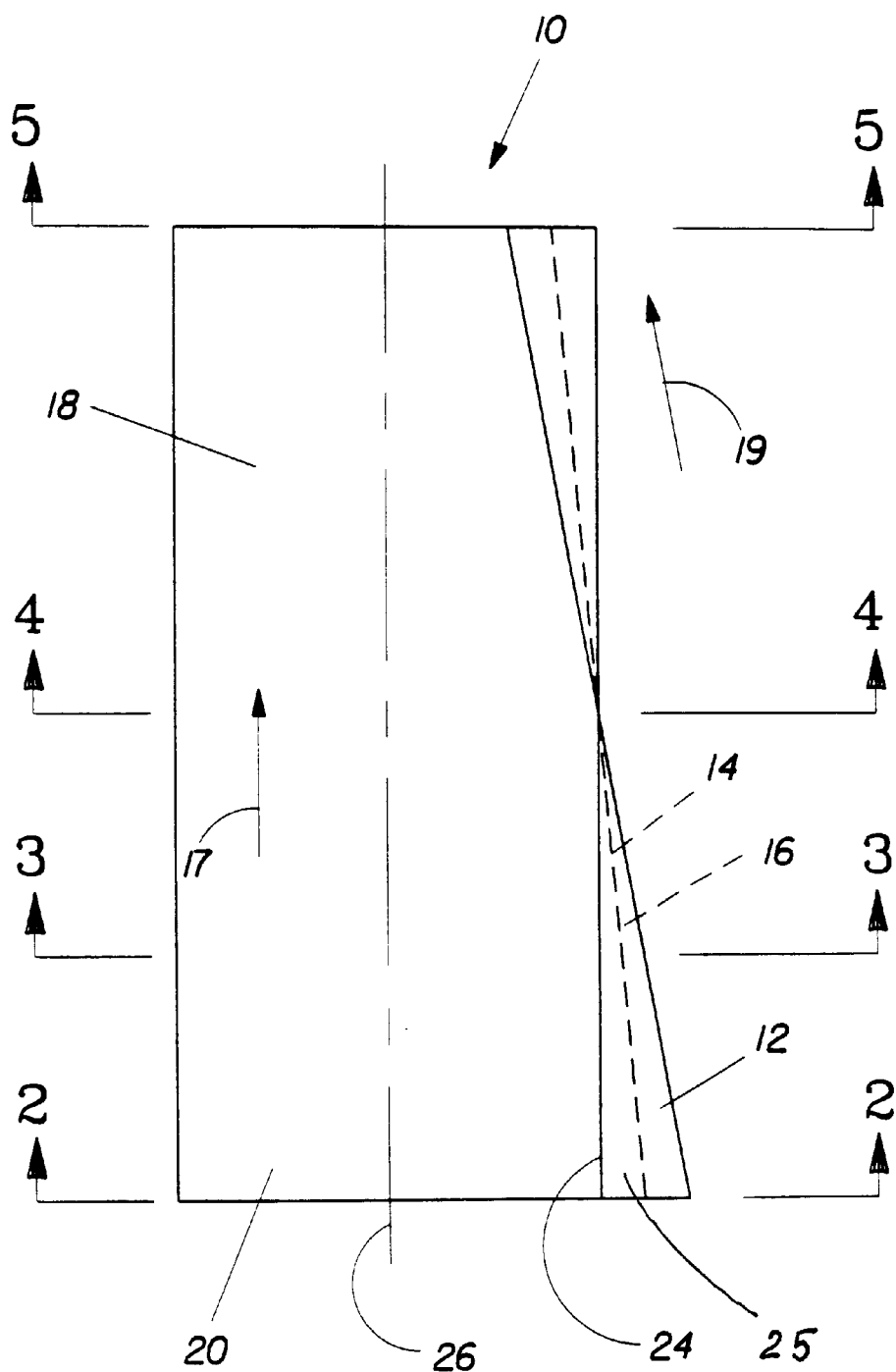
FIG. 1 is a simplified plan view from the top of a conventional embodiment utilizing a conveyor belt conveying a web and a folding belt to make a longitudinal fold in the web.
Figure 2:
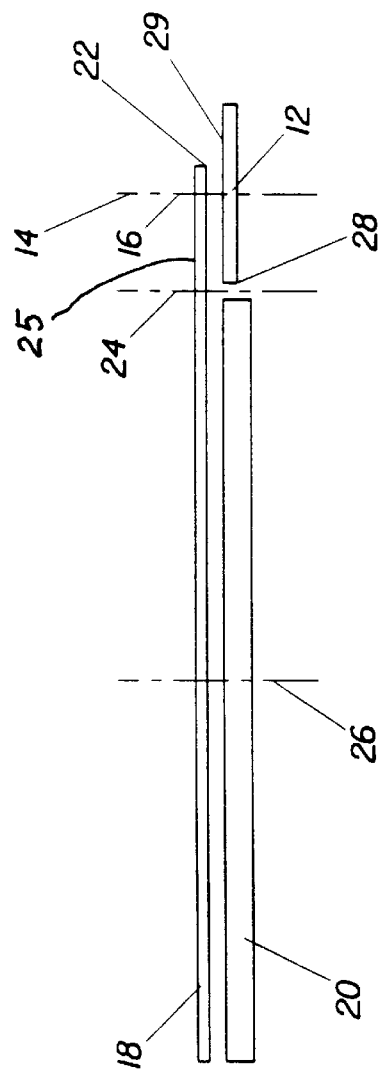
FIG. 2 is a cross-sectional view along cut line 2—2 of FIG. 1.
Figure 3:
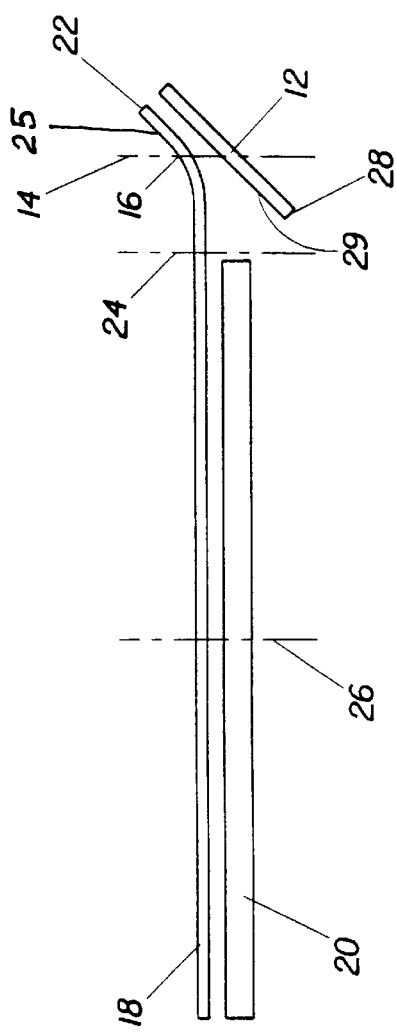
FIG. 3 is a cross-sectional view along cut line 3—3 of FIG. 1.
Figure 4:
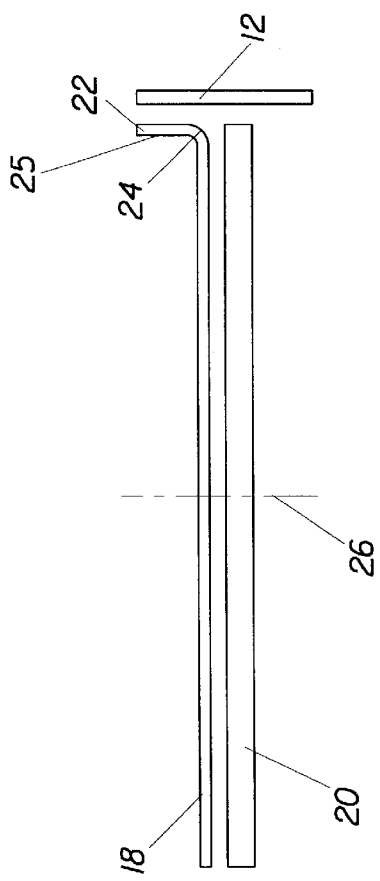
FIG. 4 is a cross-sectional view along cut line 4—4 of FIG. 1.
Figure 5:
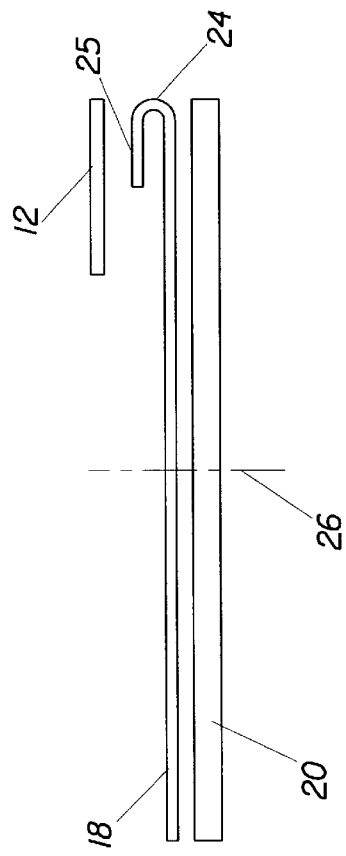
FIG. 5 is a cross-sectional view along cut line 5—5 of FIG. 1.
Figure 6:
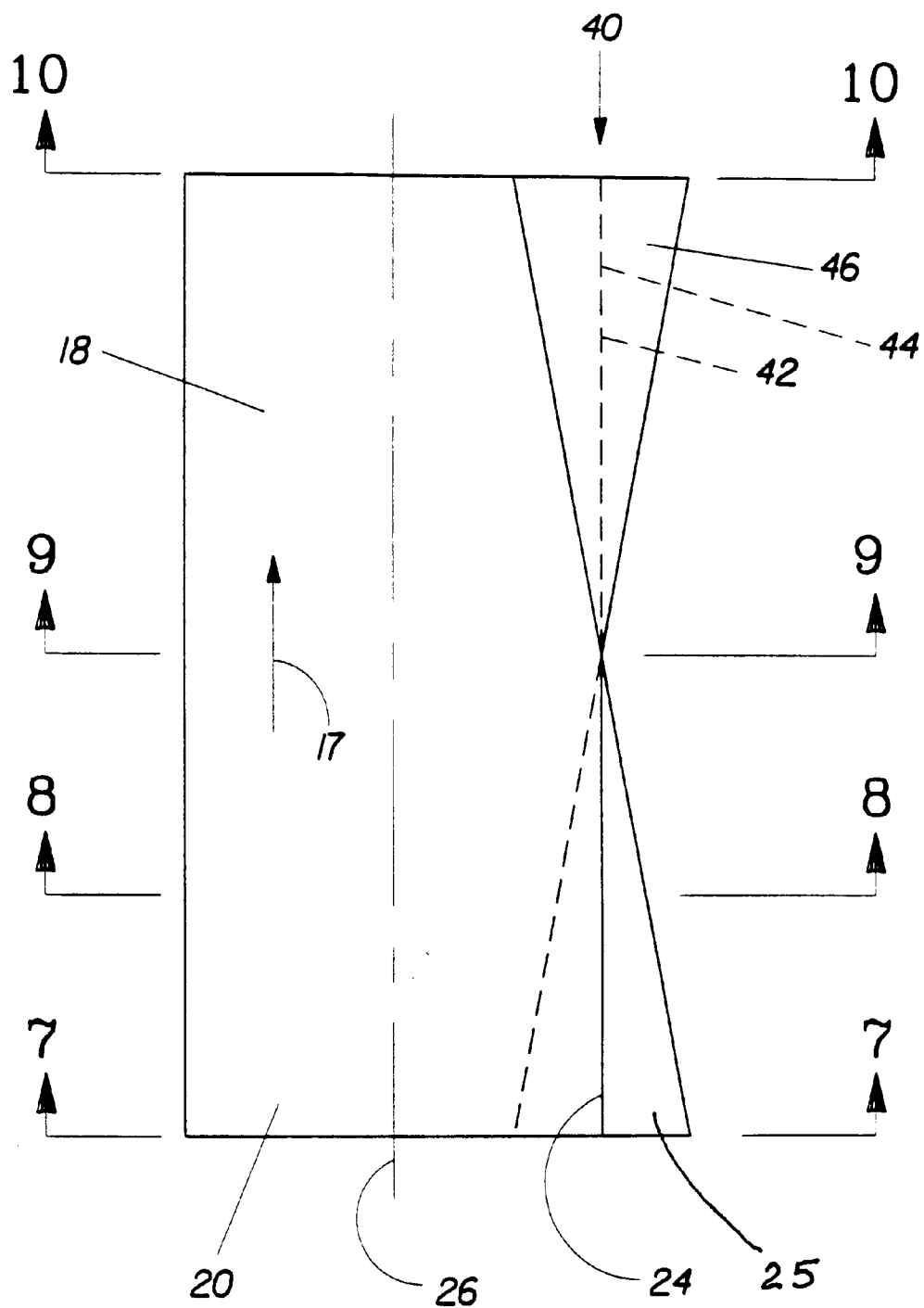
FIG. 6 is a simplified plan view from the top of one embodiment of the present invention utilizing a conveyor belt conveying a web and a simply-supported folding belt to make a longitudinal fold in the web.
Figure 11:
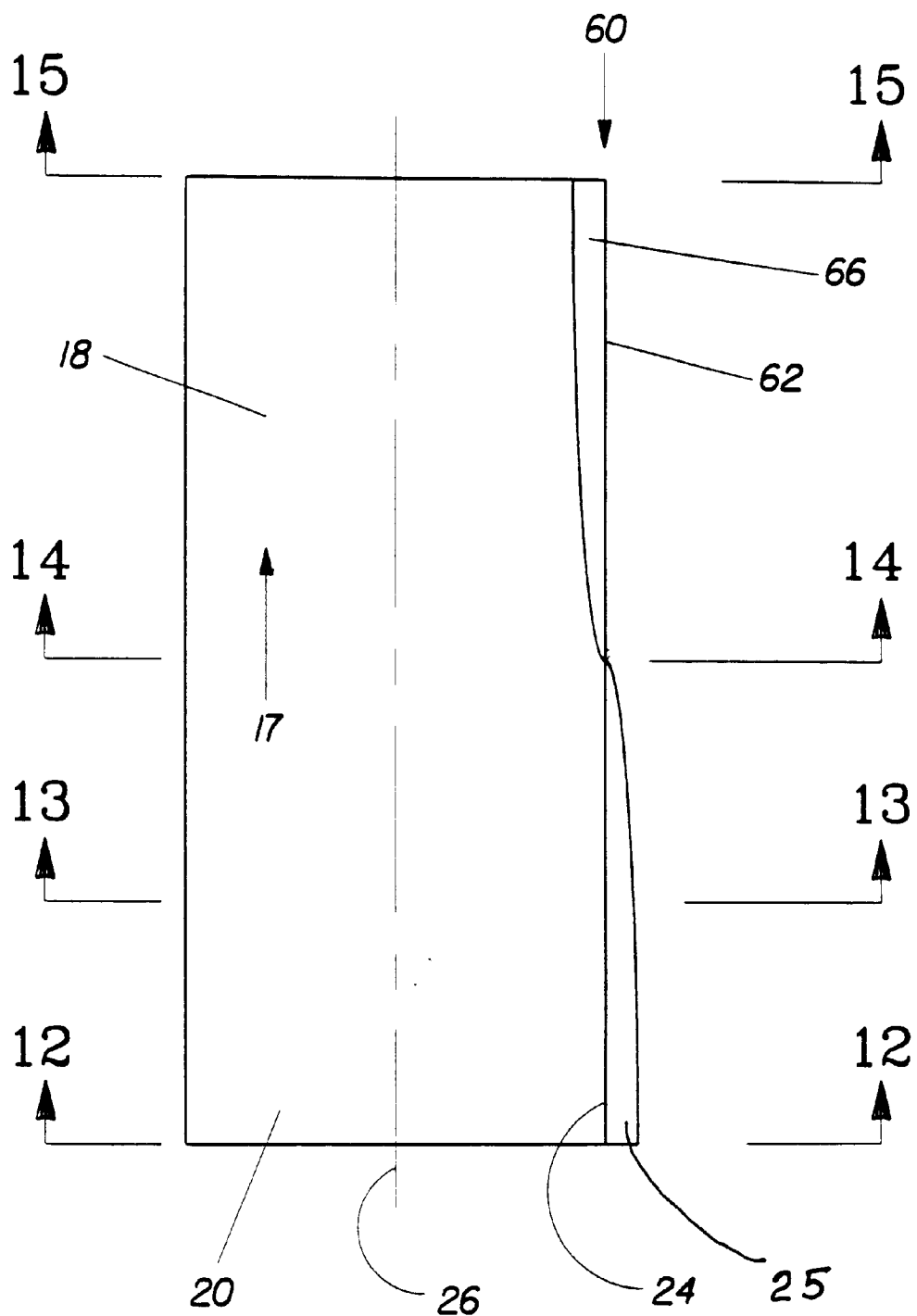
FIG. 11 is a simplified plan view from the top of another embodiment of the present invention utilizing a conveyor belt conveying a web and a simply-supported folding belt to make a longitudinal fold in the web.

It will be readily apparent to those skilled in the art that the present invention may be useful for folding nearly any web, dry or wet, having sufficient structural integrity to be processed as a continuous web. Non-limiting examples of such webs may include non-woven substrates, plastic films, foams, tissues, rubbers, metal foils and other materials, either separately or in combination, and in single or multiple-layer forms. In particular, the present invention may be useful in production of disposable absorbent articles or any garment-like product, both disposable and non-disposable, manufactured by utilizing a web having continuous or discontinuous longitudinal edges, which need to be folded.

In the following description, a "web" is any web of material which is continuous in a machine direction and which may include components that are discontinuous or discrete in the machine direction. Further, the web may comprise a single or multiple layers of materials, attached or not attached to each other. The web may also comprise a plurality of interconnected disposable absorbent articles, such as diapers or feminine hygiene articles. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article, i.e., they are intended to be discarded after a single use and, preferably, to be recycled, composted or otherwise disposed of in an environmentally compatible manner. As used herein, the term "diaper" refers to an absorbent article generally worn by infants and other incontinent persons about the lower torso. The term "feminine protection device" refers to an absorbent article worn by women to absorb and contain menses and other vaginal exudates. The term "body wrap" refers to an article or a garment worn about the body, typically to provide some therapeutic benefit, such as, for example, pain relief, wound coverage or to hold another device or article near the body. As used herein, the term "garment" refers to an article of clothing, including undergarments such as disposable diapers, training pants, incontinence briefs, incontinence undergarments, absorbent inserts, diaper holders and liners, feminine protection devices, bandages, body wraps, bibs and the like.

FIGS. 6–10 illustrate the folding belt system 40 of the present invention having a simply-supported folding belt 46. (The term "simply-supported folding belt" or "folding belt" refers hereinafter to a belt which extends between at least two opposing pulleys by wrapping at least partially around at least one of these pulleys, and which is not supported between these pulleys by an under-belt track directing the belt to rotate or twist between these pulleys.) In the system 40, contrary to the conventional art shown in FIGS. 1–5, the longitudinal axis of rotation 42 of the folding belt 46 is substantially parallel to the fold line 24 of the web 18. (The term "longitudinal axis of rotation" refers herein to an axis around which a folding belt rotates or twists during folding a longitudinal fold of a web.) Accordingly, contact between the folding belt 46 and the web 18 is maintained during the folding of the flap 25. In the system 40, the longitudinal axis of rotation 42 of the folding belt 46 generally coincides with the longitudinal centerline 44 of the folding belt 46, which is substantially parallel to the machine direction 17. (The term "longitudinal centerline" refers herein to a centerline which is equidistant between the opposing longitudinal edges of a belt.)

FIG. 7 illustrates an initial arrangement of the folding belt 46 at a zero rotation position of the folding belt 46 in relation to the conveyor belt 20 (or any other suitable web-supporting device). The folding belt 46 is preferably not coplanar with the conveyor belt 20. In the initial position, as shown in FIG. 7, the folding belt 46 is disposed generally parallel to the conveyor belt 20, however, the folding belt 46 need not be necessarily generally parallel to the conveyor belt 20; the folding belt 46 can be inclined in relation to the conveyor belt 20 as long as at least a portion of the folding belt 46 is subordinate to the conveyor belt 20. For example, the initial position of the folding belt 46 can be any position intermediate to the position of FIG. 7 and a transitional position of FIG. 8. FIGS. 9 and 10 illustrate, respectively, a 90-degree-rotation position and a final, about 180-degree-rotation position of the folding belt 46 in relation to the conveyor belt 20 and the web 18. As seen from FIGS. 8–9, the folding belt 46 and the flap 25 both rotate around the coinciding axis 42 and fold line 24 and, therefore, there is no substantial relative movement between the web-contacting surface 50 of the folding belt 46 and the flap 25. Thus, no drag is produced which may affect formation of wrinkles and/or irregularities in the shape of the folded flap 25.

Figure 12:
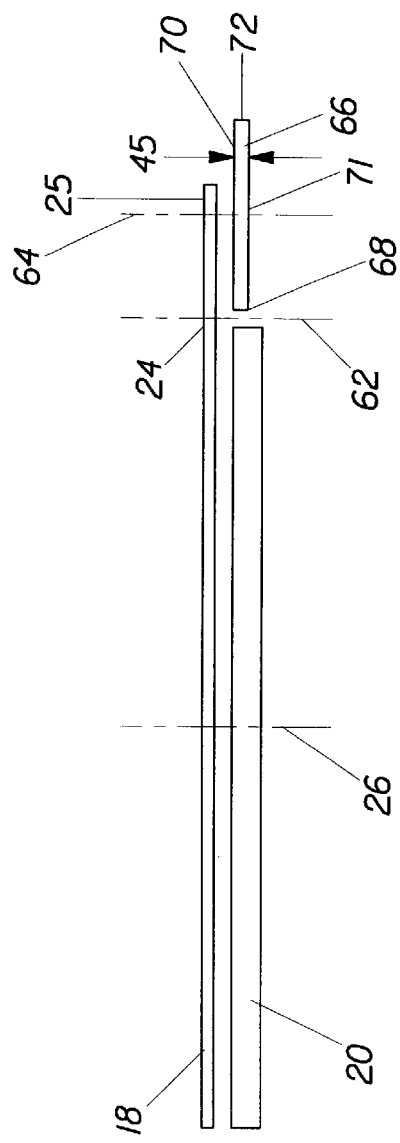
FIG. 12 is a cross-sectional view along cut line 12—12 of FIG. 11.
Figure 13:
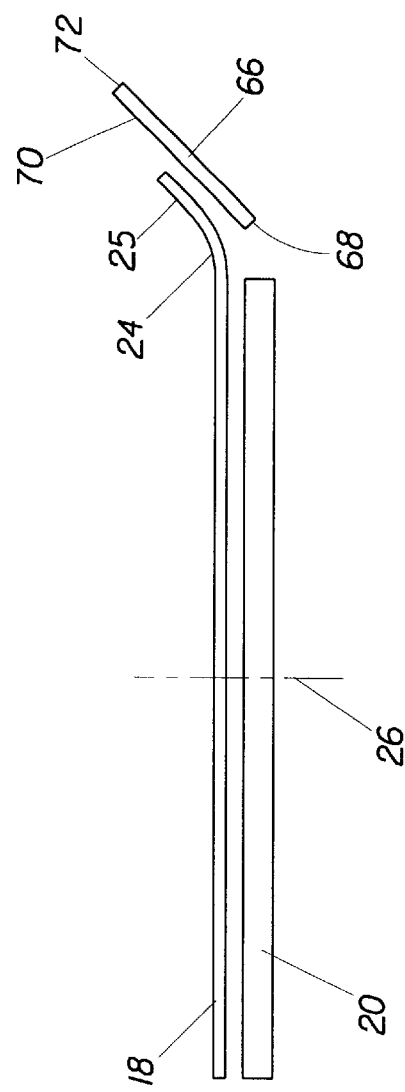
FIG. 13 is a cross-sectional view along cut line 13—13 of FIG. 11.

FIGS. 11–15 show an alternative embodiment of the present invention, wherein the folding belt system 60 includes the folding belt 66 having the longitudinal axis of rotation 62 substantially parallel to the longitudinal fold line 24 of the web 18. However, in the system 60, the longitudinal axis of rotation 62 does not coincide with the longitudinal centerline 64 of the folding belt 66, but preferably generally coincides with the first longitudinal edge 68 of the folding belt 66. FIG. 12 illustrates an initial arrangement of the folding belt 66 at a zero rotation position of the folding belt 66 in relation to the conveyor belt 20 (or any other suitable web-supporting device) and the web material 18, wherein the folding belt 66 is generally coplanar with the conveyor belt 20. FIGS. 13, 14 and 15 illustrate, respectively, an intermediate position, a 90-degree rotation position, and a final 180-degree position of rotation of the folding belt 66 in relation to the conveyor belt 20 and the web 18. As seen from FIGS. 12–15, the folding belt 66 and the flap 25 both rotate around the axis 62 and, therefore, there is no substantial relative movement between the web-contacting surface 50 of the folding belt 66 and the flap 25. Thus, again, no drag is created which may affect formation of wrinkles and/or irregularities in the shape of the folded flap 25.

In order to provide rotation of the folding belt 66 in its longitudinal direction around an axis other than its longitudinal centerline 64 (as illustrated in FIGS. 11–15), the folding belt 66 may be subjected to a non-symmetrical tension profile across the width of the folding belt 66. The term "non-symmetrical tension profile" across the belt width refers herein to a tension profile across the belt width which is not symmetrical in relation to a longitudinal centerline of the belt. The term "symmetrical tension profile" refers herein to a tension profile across the belt width which is symmetrical or has a mirror image in relation to a longitudinal centerline of the belt. The belts with symmetrical tension profiles across the belt width, when twisted by rotating the opposite ends of the belt in opposite directions, will generally twist about an axis of rotation which generally coincides with the longitudinal centerline of the belt.

Figure 16:
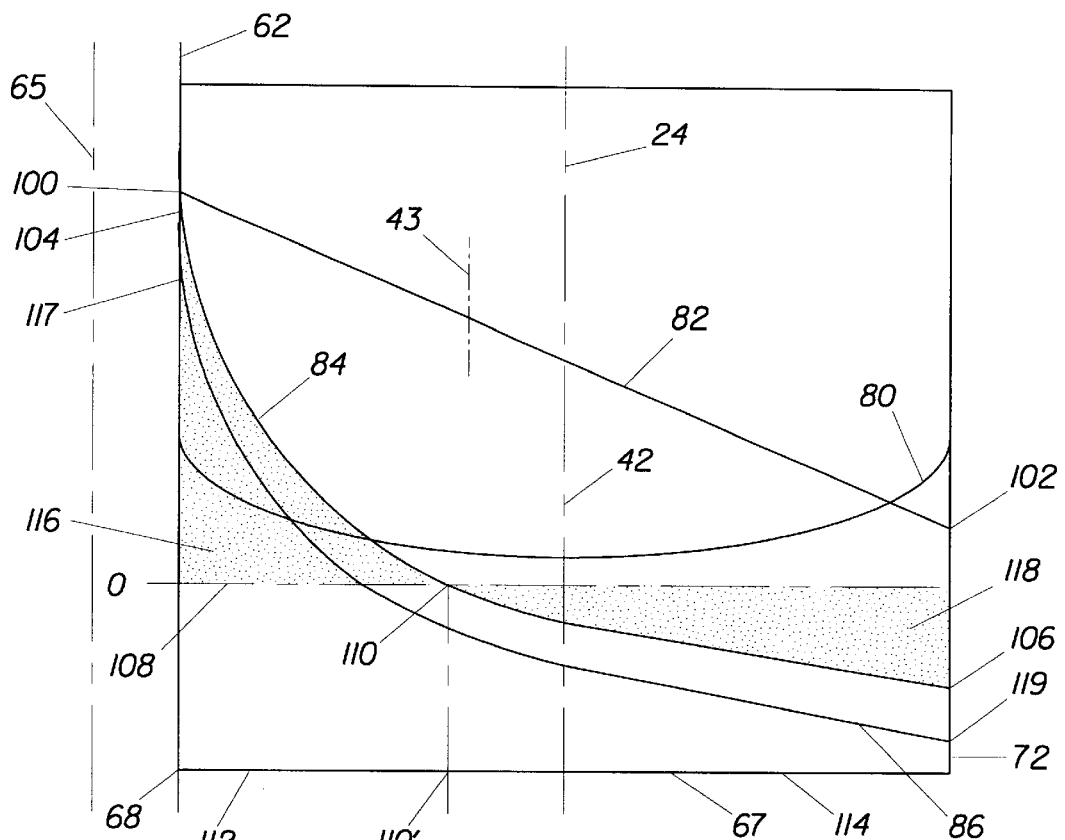
FIG. 16 is a graph illustrating tension profiles in folding belts of the present invention.

Some examples of tension profiles to which a simply-supported folding belt may be subjected are shown in FIG. 16, wherein the vertical axis represents a tension in the cross-section of the belt and the horizontal axis represents the belt width 67 extending between the first longitudinal edge 68 and the second longitudinal edge 72, and wherein the first longitudinal edge 68 is proximal to the longitudinal centerline 26 of the conveyor belt 20. One example of a symmetrical tension profile in a twisted belt is illustrated by the function 80 which is symmetrically positioned in relation to the longitudinal centerline 42. (However, any other shapes or configurations of symmetrical tension profiles in the folding belt of the present invention may be suitable.)

Examples of non-symmetrical tension profiles are illustrated by functions 82, 84 and 86 (see FIG. 16), each having the higher tension 100, 104 and 117, respectively, at the first longitudinal edge 68 and the lower tension, 102, 106 and 119, respectively, at the second longitudinal edge 72. Furthermore, the function 82 illustrates a folding belt having both edges under positive tension values 100 and 102, however, each of the functions 84 and 86 illustrates a folding belt having the positive tension value 104 and 117, respectively, on the first longitudinal edge 68 and the negative tension values 106 and 119, respectively, on the second longitudinal edge 72 extending below the zero-tension line 108. Thus, each of the functions 84 and 86 represents a twisted belt, wherein the first longitudinal edge 68 is stretched under the positive tension 104 and 117, and the second longitudinal edge 72 is compressed under the negative tension (i.e., compression) 106 and 119. The function 82 provides the axis of rotation 43, which is offset from the longitudinal centerline 24 at a distance less than half of the width 67 of the belt 66. The function 84 provides the axis of rotation 62 which is offset from the longitudinal centerline 24 a distance substantially equal to the width 67 of the belt 66. The function 86 provides an axis of rotation 65 which is offset from the longitudinal centerline 24 a distance greater than half of the width 67 of the belt 66. (It should be noted, that any other shapes or configurations of non-symmetrical tensions profiles in a folding belt of the present invention may be suitable.)

Referring to FIG. 16, the function 84 is one preferred embodiment of a non-symmetrical tension profile for the folding belt 66 of the system 60 of the present invention, wherein the folding belt 66 rotates around its first longitudinal edge 68 which generally coincides with the longitudinal axis of rotation 64. The function 84 intersects with the zero-tension line 108 at the point 110. The point 110 projects on the horizontal axis forming the point 110' which divides the width 67 of the folding belt 66 into the tension zone 112 and the compression zone 114. The tension zone 112 and the compression zone 114, respectively, define the tensile area 116 and the compressive area 118, each of which is contained between the function 84 and the zero-function line 108. In one preferred embodiment of the present invention, the tensile area 116 and the compressive area 118 are preferably substantially equal in order to provide rotation of the folding belt 66 around its longitudinal axis of rotation 64 generally coinciding with the first or shorter longitudinal edge 68 of the folding belt 66. The tensile areas 116 and 118 represent the forces causing rotation of the simply-supported folding belt 66. If the compressive area 118 is greater than the tensile area 116, a resulting force, specifically, a lateral component of this force, may affect mistracking of the folding belt 66. In contrast, if the tensile area 116 is greater than the compressive area 118, then the resulting differential force may shift the axis of rotation 64 from the first longitudinal edge 68 inward toward the second longitudinal edge 72 of the folding belt 66.

The non-symmetrical tension-profiles in a folding belt can be provided by one or more of the following factors: (1) by the belt geometry, wherein the opposing longitudinal edges of the belt are not equal in length in relaxed or untensioned state; (2) by the geometry of the opposing pulleys around which a simply-supported folding belt is wrapped during the rotation, wherein at least a portion of at least one of the opposing pulleys has a shape resembling a frustum of a cone; and (3) by the belt material properties, wherein the modulus of elasticity of the belt is varied along the belt width. However, it should be noted that the non-symmetrical tension profiles in a folding belt can be also provided by other factors. These factors may include cylindrical pulleys (with a crown or without the crown) disposed such that the cylindrical surface of the pulleys is inclined in relation to the surface of the belt to simulate the effect provided by the cone-shaped pulleys of the present invention.

Figure 19:
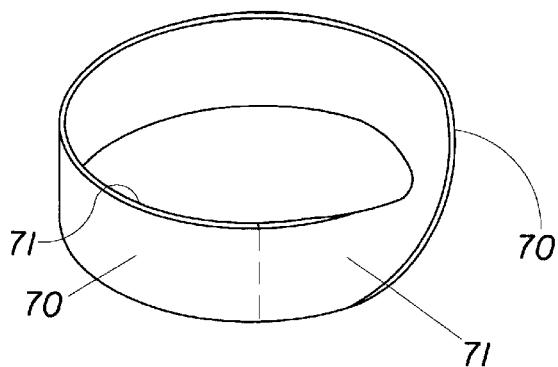
FIG. 19 is a perspective view of another embodiment of a folding belt of the present invention.

The folding belt of the present invention may be constructed as a continuous belt by any known process, such as, for example, molding, casting, thermoforming, woven or non-woven processes and the like. Further, the folding belt of the present invention may have a first surface 70 and a second surface 71 which are separated from each other by a thickness 45 of the folding belt (see FIGS. 7 and 12). Alternatively, the folding belt of the present invention may be a mobius belt (i.e., when the belt is spliced after being twisted 180 degrees such that the first surface 70 continues from the second surface 71 as shown, for example, in FIG. 19).

The folding belt of the present invention can be fabricated from any material suitable to perform the desired function of providing a suitable web-supporting or web-contacting surface of the folding belt capable of folding a longitudinal edge of the web. The folding belt materials can include materials having very wide differences in various material properties, for example, tensile strength, elasticity, stretch, flexibility, surface properties and the like. Therefore, suitable folding belt materials may include various conventional belting materials, as well as non-conventional applications of certain materials as folding belts, for example, non-woven webs and the like.

Figure 17:
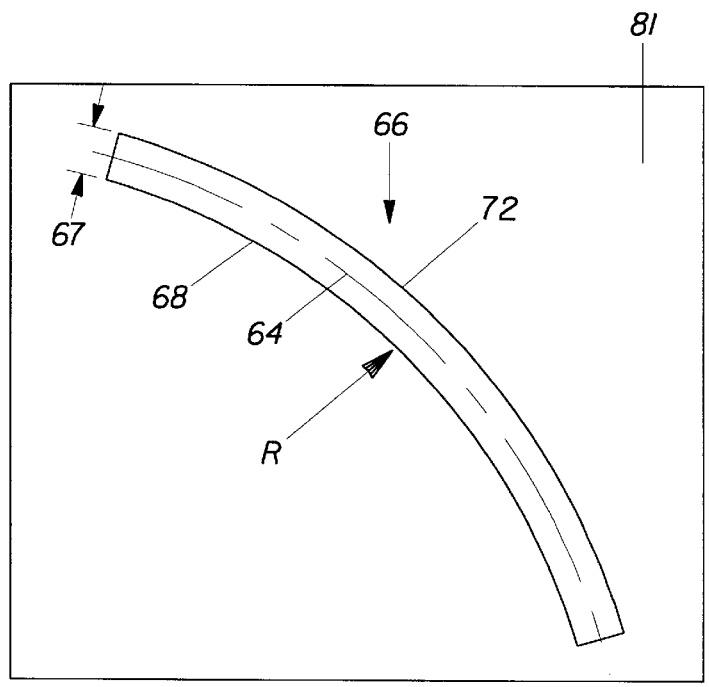
FIG. 17 is a plan view of one embodiment of a folding belt of the present invention in an unspliced form.
Figure 18:
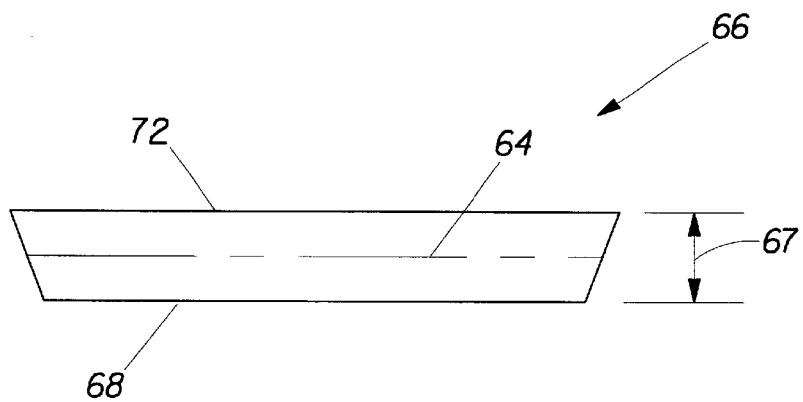
FIG. 18 is a side view of the folding belt shown in FIG. 17 after it has been spliced into a continuous belt.

In the folding belt system 60 shown in FIGS. 11–15, the non-symmetrical tension profile is provided by the geometry of the folding belt 66, wherein the first longitudinal edge 68 is shorter then the second longitudinal edge 72. One way to create the folding belt 66 is shown in FIG. 17, where the folding belt 66 is cut out from a sheet of the belt material 81 at the predetermined radius R, thus forming the curved strip of belt 82. The strip 82 is then spliced into the continuous belt 66 shown in FIG. 18 in its relaxed or untensioned state, forming a frustum of a cone. It should be noted that other ways to provide a belt having unequal longitudinal edges may include a straight belt having at least one end of the belt cut and spliced at an angle, i.e. not perpendicular to the longitudinal edge of the belt. It also should be noted that the folding belt may be spliced by any suitable method known in the art.

Referring to FIG. 17, the radius R of the simply-supported folding belt 66 can be calculated by the following equation:

$$radius = \frac{width}{\frac{\sqrt{length^2 + (flipangle \cdot width)^2}}{length} - 1}$$

wherein
width is the width 120 of the folding belt 66 which is generally selected by the width of the folded flap,
length is the length between the two opposing idlers, around which the folding belt wraps, measured between the centers of rotation of the opposing idlers, flipangle is the degree of rotation which the folding belt makes in providing a fold, for example, from the initial position of the folding belt 66 shown in FIG. 12 to the final position shown in FIG. 15.

The tension profile in the folding belt 66 can be calculated by the following equation:

$$tension = \int_0^{width} \left[ \frac{elong + length}{\sqrt{length^2 + (flipangle \cdot width)^2}} - 1 \right] E_M \cdot d\,width$$

wherein
elong is the difference in length between stretched and unstretched conditions of the shorter longitudinal edge of the folding belt (the first longitudinal edge 68 of the folding belt 66),
$E_M$ is a modulus of elasticity of the folding belt material.

In one embodiment of the present invention the radius R of the folding belt 66 preferably ranges from about 500 mm to about 5,000 mm, and more preferably from about 800 mm to about 1,800 mm. The width 67 of the folding belt 66 preferably ranges from about 10 mm to about 150 mm, and more preferably from about 10 mm to about 40 mm.

In use, the folding belt 66 of the present invention wraps around pulleys defining a continuous path of the folding belt 66. One embodiment of the pulleys of the present invention is represented by a pulley 200 shown in FIG. 20. The pulley 200 is shaped preferably as a frustum of a cone having the smaller diameter 202, the larger diameter 204, and the width 206. The diameters 202 and 204 and the width 206 could have any suitable dimensions. In a preferred embodiment of the present invention, the smaller diameter 202 is preferably about 50 mm, the larger diameter 204 is preferably about 50.6 mm, and the width 206 is preferably about 20 mm, which is generally equal to the width 67 of the folding belt 66. Further, the pulley 200 also preferably includes chamfers or fillets 208 on both sides of the width 206 of the pulley 200. In any case, the pulley 200 can be fabricated from any suitable material, for example, metals, plastics and the like. In one preferred embodiment of the present invention, the pulley 200 is fabricated from an anodized aluminum.

Figure 21:
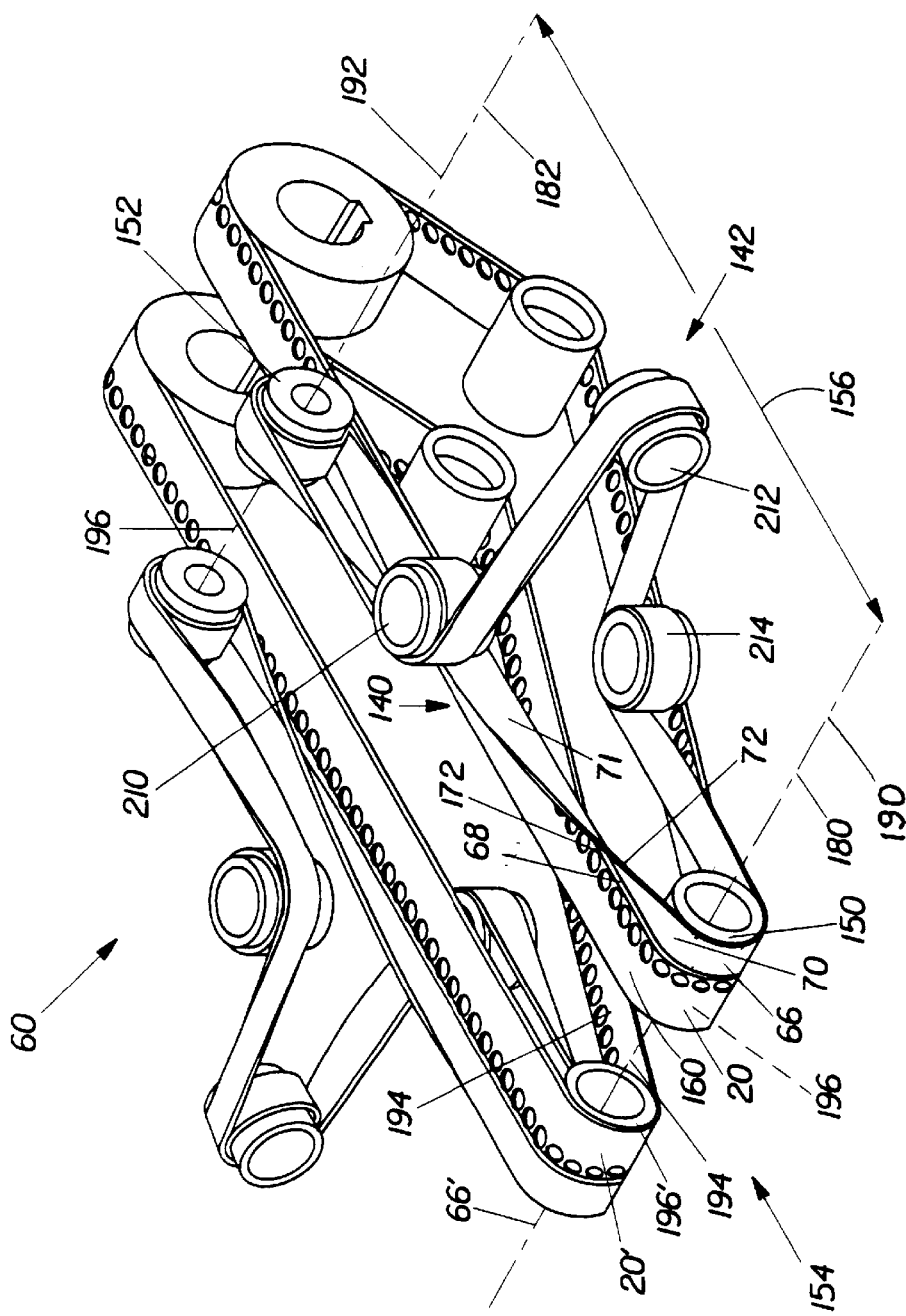
FIG. 21 is a perspective view of the embodiment of the present invention shown in FIG. 11.

The folding belt system 60 of FIGS. 11–15 is also illustrated in a perspective view in FIG. 21, wherein folding belts 66 and 66' fold both longitudinal folds of the web 18 carried by conveyor belts 20 and 20'. (It should be noted that the number of conveyor belts carrying the web can be any suitable number that ranges from a single belt to multiple belts.) The conveyor belts 20 and 20' preferably include vacuum holes to provide accurate positioning of the fold line 24 of the web 18. However, the web 18 may be held by any suitable means including but not limited to mechanical grippers, high coefficient friction areas, electrostatic charges, compressed air jets and/or combinations thereof. Similarly, if desired, the one or more folding belts 66 and 66' may include any suitable web-holding means, for example, mechanical grippers, high coefficient friction areas, electrostatic charges, compressed air jets and/or any combination thereof. Each of the folding belts 66 and 66' may have similar configuration, therefore, for simplicity of explanation, the invention will be described for a single folding belt 66 configuration.

Figure 20:
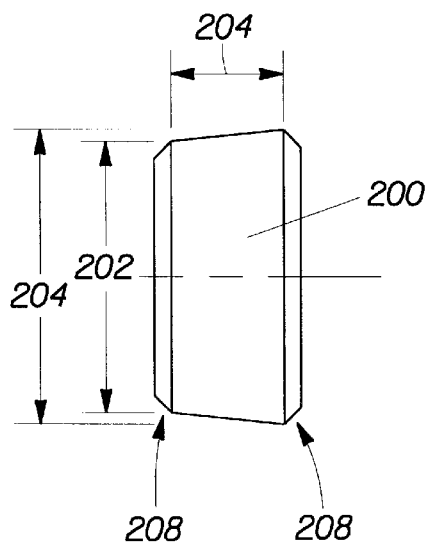
FIG. 20 is a side view of a folding belt pulley used in the present invention.

Referring to FIG. 21, the folding belt 66 moves in a continuous path that includes the folding path 140 and the returning path 142. The folding path 140 extends in the direction of the web path 154 from the starting folding position 190 to the finished folding position 192. The starting folding position 190 coincides with the axis 180 of the first pulley 150. The finished folding position 192 coincides with the axis 182 of the second pulley 152. (These pulleys are illustrated in FIG. 20 as pulley 200.) The first pulley 150 is disposed adjacent to the first longitudinal edge 172 of the conveyor belt 20 such that, in the starting folding position 190, the web-contacting surface 160 of the conveyor belt 20 is generally coplanar with the web-contacting surface 70 of the folding belt 66. The second pulley 152 is disposed such that the web-contacting surface 70 of the folding belt 66 faces the web-contacting surface 160 of the conveyor belt 20 and is separated by the gap 31 (see FIG. 15) which is generally equal to the combined thickness of the folded web 18. Further, the second pulley 152 is disposed such that the first longitudinal edge 68 of the folding belt 66 remains substantially parallel to the first longitudinal edge 172 of the conveyor belt 20. Further, the first pulley 150 and the second pulley 152 are disposed such that the larger diameter 204 (see FIG. 20) of the pulleys 150 and 152 is aligned with the shorter or first longitudinal edge 68 of the folding belt 66.

The first and second pulleys 150 and 152, respectively, are preferably separated along the web path 154 by a folding length 156. The folding length 156 may be selected from a desired length-to-width ratio between the folding length 156 and the width 67 (see FIG. 17) of the folding belt 66. The length-to-width ratio preferably ranges from about 3 to about 50, and more preferably from about 5 to about 20. In the folding belt system 60, the length-to-width ratio is preferably about 18, the belt width 67 is preferably about 20 mm, and the folding length 156 is preferably about 360 mm. Further, along the folding length 156, the folding belt 66 preferably rotates about 180 degrees at a rate of rotation of 0.5 degrees per mm. The term "rate of rotation" refers herein to a ratio between a degree of rotation or twisting of a folding belt extending between two opposing pulleys (around which the folding belt wraps) and a length between the axes of rotation of the two opposing pulleys.

As shown in FIG. 21, the axis 190 of the first pulley 150 of the folding belt 66 coincides with the axis 194 of the first pulley 196 of the conveyor belt 20. However, it should be noted that the axis 190 need not necessary coincide with the axis 194.

Referring to FIG. 21, the returning path 142 of the folding belt 66 can take any suitable configuration such that it does not disturb the required tension profile of the folding belt 66 in the folding path 140. Because the tension profile of the folding belt 66 is generally dependent upon the rate of rotation of the folding belt 66, it is preferred to maintain a substantially equal rate of rotation throughout the length of the folding belt 66, which includes the returning path 142. The returning path 142 can be defined by any suitable number of pulleys. In one preferred embodiment of the present invention shown in FIG. 21, there are three returning path pulleys 210, 212 and 214 defining the returning path 142. The returning pulleys 210, 212 and 214 can have any suitable shape and dimensions, and can be manufactured from any suitable material. In one preferred embodiment of the present invention, the returning pulleys 210, 212 and 214 preferably have the same shape and dimensions as the pulleys 150 and 152 from the folding path 156. Further, similarly to the pulleys 150 and 152, the returning pulleys 210, 212 and 214 are disposed such that the larger diameter 204 (see FIG. 20) of the pulleys is aligned with the shorter or first longitudinal edge 68 of the folding belt 66.

The simply-supported folding belt pulleys and the conveyor pulleys described herein may be arranged and rotatably supported within a suitable frame, and conventional drive mechanisms are operatively connected thereto employing ordinary techniques well known to a person skilled in the art.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method for making a longitudinal fold in a web, the method comprising the steps of:
   (i) providing a web-supporting device comprising a web-contacting surface, a first longitudinal edge and a second longitudinal edge opposed thereof;
   (ii) providing a simply-supported folding belt disposed adjacent to the first longitudinal edge of the web-supporting device, the simply-supported folding belt comprising a first surface contacting the web, a first longitudinal edge and a second longitudinal edge opposed thereto, a width extending between the first and the second longitudinal edges, a longitudinal centerline and a longitudinal axis of rotation which is generally parallel to the longitudinal centerline, wherein the first longitudinal edge is shorter than the second longitudinal edge in relaxed state and wherein the first longitudinal edge is defined by a radius;
   (iii) providing the web having a first longitudinal edge and a second longitudinal edge opposed thereto, the web being superimposed onto the web-contacting surface of the web-supporting device such that the first longitudinal edge of the web extends laterally beyond the first longitudinal edge of the web-supporting device and at least partially onto the first surface of the simply-supported folding belt; and
   (iv) folding the longitudinal fold of the web by twisting the simply-supported folding belt around its longitudinal axis of rotation such that the first surface of the simply-supported folding belt rotates around the first longitudinal edge of the web-supporting device to at least partially face the web-contacting surface of the web-supporting device, wherein the longitudinal axis of rotation of the simply-supported folding belt extends substantially parallel to a longitudinal fold line of the longitudinal fold of the web,
   wherein the simply-supported folding belt further comprises a second surface opposed to the first surface of the simply-supported folding belt, and wherein the second surface is separated from the first surface by a thickness of the simply-supported folding belt.

* * * * *